United States Patent [19]

Takatsuki

[11] 3,931,815

[45] Jan. 13, 1976

[54] ASSEMBLY HAVING AN ADAPTER AND A HOLDER WITH A DOUBLE ENDED NEEDLE

[75] Inventor: Nobuyuki Takatsuki, Tokyo, Japan

[73] Assignee: Jintan Terumo Company, Ltd., Tokyo, Japan

[22] Filed: Jan. 2, 1975

[21] Appl. No.: 538,152

Related U.S. Application Data

[63] Continuation of Ser. No. 392,565, Aug. 29, 1973, abandoned.

[52] U.S. Cl. ........ 128/2 F; 128/DIG. 5; 128/218 D; 128/276
[51] Int. Cl.² ............................................ A61B 5/14
[58] Field of Search... 128/DIG. 5, 2 F, 276, 218 D, 128/218 R, 218 NV, 218 P, 218 PA, 220, 215, 216, 219

[56] References Cited
UNITED STATES PATENTS

| | | | |
|---|---|---|---|
| 1,343,085 | 6/1920 | Lerch | 128/218 P |
| 2,233,554 | 3/1941 | Pletcher | 128/218 D X |
| 2,688,325 | 9/1954 | Lockhart | 128/218 P |
| 2,688,965 | 9/1954 | Huber | 128/218 D |
| 2,888,923 | 6/1959 | Da Cunha Reis | 128/218 D |
| 2,888,924 | 6/1959 | Dunmire | 128/218 D |
| 3,304,934 | 2/1967 | Bautista | 128/DIG. 5 |
| 3,366,103 | 1/1968 | Keller | 128/DIG. 5 |
| 3,724,460 | 4/1973 | Gomez et al | 128/PA |
| 3,734,080 | 5/1973 | Petterson | 128/DIG. 5 |

*Primary Examiner*—Kyle L. Howell
*Attorney, Agent, or Firm*—Kemon, Palmer & Estabrook

[57] ABSTRACT

An assembly comprising a holder having one open end, a double ended needle fixed to a closed end of the holder and an adapter detachably insertible into the holder, the use of the adapter of the same or varying size permitting an exchange of one fluid sample container or medicament container for another with the needle pierced into the blood vessel of the human body for injection or blood collection.

1 Claim, 8 Drawing Figures

ASSEMBLY HAVING AN ADAPTER AND A HOLDER WITH A DOUBLE ENDED NEEDLE

This is a continuation, of application Ser. No. 392,565, filed Aug. 29, 1973, now abandoned.

This invention relates to an assembly comprising a holder having one open end, a double-ended needle fixed to a closed end of the holder and an adapter detachably insertible into the holder.

A variety of assemblies for injection or blood collection which consist of a holder and a needle have been proposed up to this date. A representative example is an assembly consisting of a holder and a double-ended needle. The use of a holder and a double-ended needle permits an exchange of one fluid sample container or medicament container for another with the needle pierced into the blood vessel of the human body. As a result, blood collection and injection can be effected at the same time.

However, the blood fluid sample container or medicament container is not always of the same size. Recently, a simultaneous blood collection has been effected in an attempt to examine a blood cell count, blood sugar, sedimentation rate of erythrocyte, coagulation of blood etc. The amount of blood to be collected, as well as the medicaments sealed into the container, is varied dependent upon the kind of examinations.

There is often required the simultaneous use of containers conforming to the inner diameter of the holder and containers smaller in size than the inner diameter of the holder. In the case of the conventional holder, difficulty is presented in piercing the center of the container with a needle and a certain amount of skill is required. As a result, blood collection may be unsuccessful.

Repetition of a blood collection can be painful to a patient and require additional expense and time. These problems can be overcome using an assembly according to this invention.

According to the invention, an assembly comprises a holder having an open end and closed end, a double-ended needle fitted to the closed end of the holder through a hub and having one end projected into the holder and the other end projected outside the holder, an elastic sheath enveloping the needle projected into the holder, and an adapter having an open end and a closed end and adapted to be detachably inserted into the holder, said adapter having at its closed end a bore through which the needle enveloped with the elastic sheath is freely insertible and at its open end a flange, wherein where the adapter is inserted into the holder a clearance is created between the closed end of the holder and the closed end of the adapter to such an extend that, when a container is inserted into the adapter, said one end of the needle can pierce through the container for communication therewith and the bunching or collapse of the elastic sheath as encountered during the piercing is sufficiently allowed.

This invention will be more fully described with reference to the accompanying drawings, in which.

Figure 1:
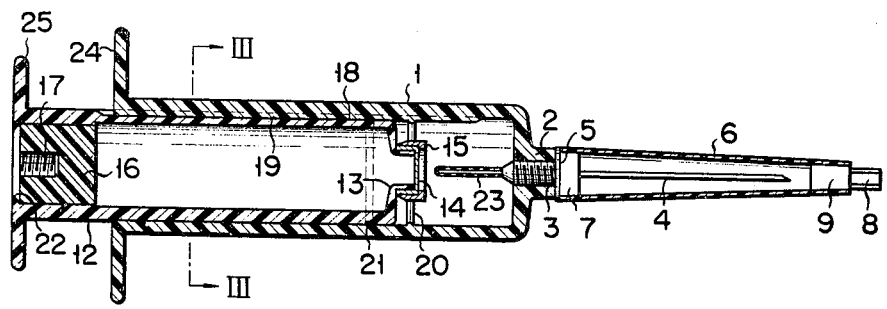
FIG. 1 is a syringe assembly including a holder with a double ended needle.
Figure 2:
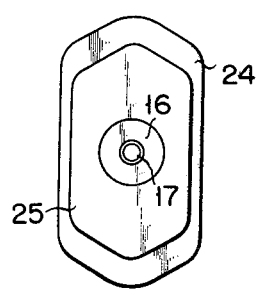
FIG. 2 is an end view of the syringe assembly of FIG. 1.
Figure 3:
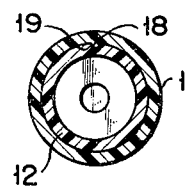
FIG. 3 is a cross sectional view through a line III—III of FIG. 2.

In FIG. 1 a reference numeral 1 is a holder made of a transparent synthetic resin and having a bottomed cylindrical configuration. At the central portion of the bottom of the holder is provided a holder projection. A reedle 4 is detachably mounted through a needle base 3. That is, the needle is fixed to the needle base and the needle base 3 is inserted into the hole of the projection 2. The needle is sharp-pointed at both ends. One end of the needle extends outwardly and the other end of the needle extends into the interior of the holder 1. At one end of the needle base a flange 5 is provided. To the outer end of the flange is mounted a mounting section 7 over which needle cover 6 is fitted. The needle cover is gradually tapered to provide a cylindrical configuration. The large-diametered open end of the needle cover is fitted over the mounting section 7. Into the small-diametered open end of the needle cover is fixed a blocking member 9 having a screw threaded engaging section 8. The engaging section 8 may be screw threaded into a piston 16 of a container 12 so that the needle cover is later used as a plunger.

An open-ended container is slidably inserted into the holder 1. The container 12 is used as a fluid sample container or a medicament container as will later be described. The container 12 has a projecting mouth 13 smaller in diameter than the body thereof. An elastic film 14 covers the small-diametered mouth 13. The outer pheriphery of the elastic film 14 is pressed onto the outer periphery of the mouth 13 by a heat shrinkable film 15.

A piston 16 is intimately fitted into the interior of the container 12. The piston can be freely moved in an airtight manner within the container. Into the outer end of the piston 16 is provided an engaging hole 17 into which the screw engaging section 8 of the needle cover is screw threaded. When the needle cover is screw-threaded into the piston 16, then the piston 16 can be slidably moved.

To prevent rotation of the piston in mounting the needle cover 6 to the piston 16, a groove 18 is provided in an axial direction of the container 12 to permit it to be engaged with a groove 19 provided on the inner surface of the holder 1. That is, the container 12 is movable in the axial direction, but it is prevented from rotation since the streak is engaged with the groove provided lengthwise of the container 12. A groove may be provided on the container and in this case a groove is provided in the holder 1. A stopper projection 20 is provided on the inner surface of the holder 1 to prevent the container 12 from being pushed into the holder to a more than necessary extent such that the elastic film 14 is prematurely pierced by the needle. Therefore, the container is not further pushed into the holder until a certain amount of force is applied. When the container is further forced into the holder to cause the needle to pierce the elastic film 14, then the projection stopper 20 is engaged with a groove 21 provided around the container 12 to impart a shock to the user, thus being stopped. The user then knows that piercing is attained.

Since the holder is made of a synthetic resin, the container 12 can be forced into the holder 1 to cause the projecting stopper 20 to be engaged with the groove 21. The piston 16 is more intimately fitted into the container than the other parts. The presence of a projection 22 provided on the open end portion of the piston 16 prevents the piston 16 from being withdrawn from the container 12. Such an arrangement prevents the piston 16 from being withdrawn from the container due to an injection pressure of a medicament, even when the container is used as a medicament container.

The end of the needle 4 projecting within the holder 1 is entirely covered with an elastic sheath 23. That is, the needle 4 is pierced first through the elastic sheath 23 and then through the elastic film 14. Since the end of the needle 4 is covered with the elastic sheath until piercing is attained, the needle is sanitarily protected from contamination. When the needle 4 is withdrawn from the elastic film 14 in an attempt to collect blood, then an elastic sheath 23 again covers the needle and prevents blood from being flowed out. Reference numerals 24 and 25 are flanges respectively provided, for convenience of operation, at the end of the holder and at the end of the container 12.

When the assembly is used as a syringe, a fluid medicament is preliminarily introduced into the container 12 . . . called as a cartridge type method, or a fluid medicament is suctioned into the container at the time it is used. In the former cartridge type method, a number of fluid medicaments are stocked within the medicament containers 12 at a factory etc. and prepared as cartridges. In practical application, the container 12 is inserted into the holder 1 to cause the needle 4 to be pierced through the elastic film 14. In this case, the projecting stopper 20 is fitted into the groove 21 of the container 12. Then, the needle cover 6 is connected to the piston 16 so that the piston can be operated through the needle cover 6. The needle 4 is pierced into the flesh of the human body using a conventional method. The piston 16 is pushed into the container through the needle cover 6 to permit the fluid medicament to be injected.

In the latter method, a fluid medicament is suctioned into the container 12. When the piston 16 is moved in a withdrawing direction, a negative pressure is created within the container 12 to permit a fluid medicament to be suctioned through the needle 4. The next procedures are the same as a cartridge type method.

When the assembly is used as a fluid collection device, the needle 4 is pierced through the elastic film 14 and the needle cover 6 is connected to the piston 16 and the piston is deeply pushed forward. Then, the needle is pierced into the blood vessel of the human body by holding a holder 1. When the piston 16 is withdrawn through the needle cover 6, a negative pressure is created within the container 12 to permit blood to be suctioned. When a blood collection is terminated the container is withdrawn from the holder 1 and the needle 4 is withdrawn from the elastic film. The hole created in the elastic film is automatically flocked by its own resiliency and no leakage is involved.

Figure 4:
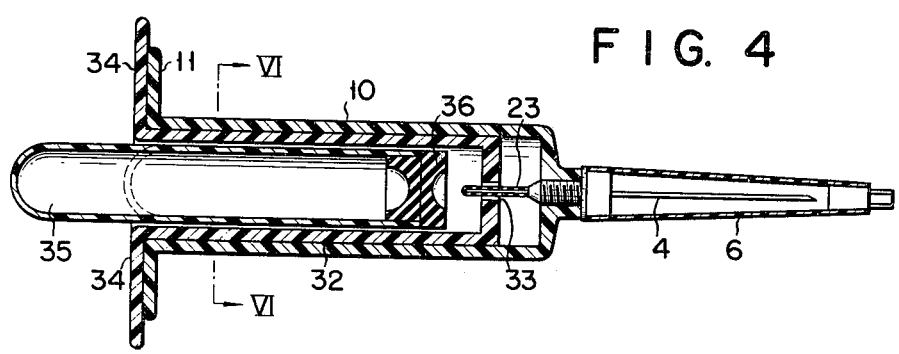
FIG. 4 is an assembly including an adapter and a holder with a double ended needle.

Explanation is now made of an embodiment of FIG. 4 in which an adapter is used in association with a holder having no groove. Where the outer diameter of the container, or what is called a fluid sample container, or a medicament container, is smaller than the inner diameter of the holder 10, an adapter 32 as shown in FIG. 4 is used. The adapter is formed in the tubular form. In the inserting end of the adapter 32 is provided a through bore for passing the needle therethrough. The adapter has a flange 34 at the outer end. Within the adapter 32 a fluid sample container 35 or a medicament container (not shown) is inserted. The container 35 is plugged by an elastic stopper 36 with a vacuum left. A needle 4 can pierce through the elastic stopper 36. Since the needle is covered by an elastic sheath 23 any number of containers may be replaced.

Figure 5:
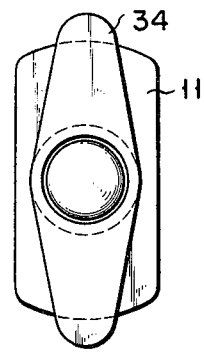
FIG. 5 is an end view of the assembly of FIG. 4.
Figure 6:
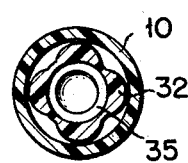
FIG. 6 is a cross sectional view through a line VI—VI of FIG. 4.

The adapter 32 has at one end a through hole 33 through which the elastic sheath covered needle can be freely inserted. At the open end of the adapter 32 are provided the flanges partly flared out beyond a flange 11 of the holder as shown in FIG. 5. The adapter has a cross section as shown in FIG. 6. The ribbed surface of the adapter is freely slidable within the holder. The adapter has a tubular hole circular in cross section into which a fluid sample container or a medicament container is slidably inserted. The adapter has the following advantages. That is, when blood is collected several times from the same person, it is possible to accurately pierce the center of the stopper 36 fitted at one end of the container. The fluid sample container is required to have its inside kept at vacuum. To facilitate the piercing of the needle, the shape as shown at 36 is adapted as an elastic stopper structure. Though it is not impossible to pierce the central thin portion of the stopper without using the adapter, a certain amount of skill is required. If the piercing is inadvertently effected in a manner to be deviated from the center of the stopper, then blood collection fails, giving pains to the human body. Secondly, the flange of the adapter is fared out beyond the flange 11 of the holder. When a small-dimensioned fluid sample container as shown by dotted lines in FIG. 4 is used, it is possible to easily withdraw the adapter with the container from the needle after blood collection. Difficulty is presented in removing the small-diametered container from the holder without using the adapter. Thirdly, when the adapter is inserted into the holder a clearance is created between the closed end of the holder and the closed end of the adapter to such an extent that when a container is inserted into the adapter the elastic sheath covered needle can pierce through the container for communication and the bunching of the elastic sheath as encountered during the piercing is sufficiently allowed. The adapter is ring-like in cross section and may take any other outer configuration.

The adapter is required to be transparent or translucent and is desirably made of the same material as that of the holder. For example, polypropylene is preferably used for such a purpose.

Blood collection can be reliably effected using the assembly including the adapter and the holder with the double-ended needle. That is, blood collection is smoothly carried out without giving any unpleasant feeling to the human body by merely exchanging one container for another, or exchanging one adapter for another so that any size of fluid sample containers or medicament containers may be used. According to this invention, therefore, replacement of the adapter can be effected with the needle pierced into the blood vessel of the human body.

Though a single projecting stopper 20 is used as shown in FIG. 1 as being engaged with the groove 21, a plurality of projecting stoppers may be used. The arrangement of the projecting stoppers may be such that the needle is pierced through the elastic film 14 when the second stopper, or any subsequent stopper, is engaged with the groove 21. The arrangement of such stoppers prevents the container 12 from being jolted within the holder.

The needle cover 6 may be bayoneted into the piston 16 or the connection of the needle cover to the piston may be effected through any other engaging means.

Figure 7:
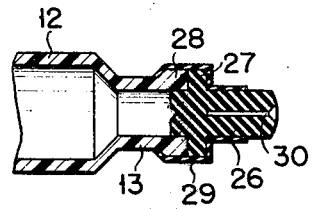
FIG. 7 is a partially cross sectional view showing another structure of an elastic sheath of FIG. 1.
Figure 8:
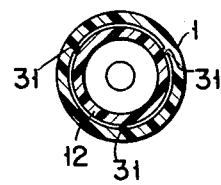
FIG. 8 is a cross sectional view showing another embodiment of FIG. 1.

Though an elastic film is used as means for sealing one open end of the container 12, an elastic stopper 26 as shown in FIG. 7 may be used as such. That is, the elastic stopper 26 has a collar 27 in contact with a flange 28 provided at the mouth of the container. Over the outer peripheral surfaces of the collar 27 and the flange 28 a heat shrinkable film 29 is fitted. The thick elastic stopper 26 has a guide hole 30 through which the needle is guided to a certain depth.

Since it is difficult to manufacture a holder and a container in a manner that the container is intimately moved relative to the holder, they are usually manufactured with a certain allowance left. In an attempt to avoid any jolt, a plurality of ribs or projections 31 may be provided.

What is claimed is:

1. A multiple sampling assembly comprising:
   a tubular container having a closed end and an open end to which a stopper is sealingly attached;
   a tubular container holder having an open end receiving said container, and a closed end to which a double-ended needle is fitted, one end of the needle being projected into the interior of the holder for piercing through the stopper into the interior of the container and the other end projected outside the holder;
   a self-recoverable elastic sheath enveloping said one end of the needle and serving as a seal against the passage of a liquid from a vein, but being pierceable by the one end of the needle when the container is positioned for injection or sampling; and
   a substantially cylindrical adapter detachably and slidably inserted in the holder receiving and keeping said tubular container substantially coaxial with said holder, said adapter having open and restricted ends, a plurality of circumferentially spaced ribs on the outer periphery thereof, an opening extending centrally through said restricted end and dimensioned to freely receive said one end of the needle and the elastic sheath therethrough, and means limiting the insertion of the adapter into the holder to a predetermined position relative to the holder, whereby to ensure between the closed end of the holder and the restricted end of the adapter a clearance sufficient to allow collapsing of the elastic sheath on piercing of said container by said one end of the needle, the inner diameter of the adapter being slightly larger than the outer diameter of the tubular container and the outer diameter of the adapter being slightly smaller than the inner diameter of the holder thereby to ensure the insertion of the tubular container into the holder in a position substantially coaxial with the holder, said adapter and container being removable from said holder to permit the holder to receive another tubular container of larger diameter.

* * * * *